[19] United States Patent
Lawson

[11] 4,083,765
[45] Apr. 11, 1978

[54] POLYMERIC ELECTROLYTIC HYGROMETER

[75] Inventor: Daniel D. Lawson, Arcadia, Calif.

[73] Assignee: The United States of America as represented by the Administrator of the National Aeronautics and Space Administration, Washington, D.C.

[21] Appl. No.: 752,748

[22] Filed: Dec. 21, 1976

[51] Int. Cl.² .............................................. G01N 27/46
[52] U.S. Cl. ................................ 204/195 W; 73/336.5
[58] Field of Search .............. 204/1 T, 195 R, 195 W; 73/335, 336.5

[56] References Cited

U.S. PATENT DOCUMENTS

| 3,001,918 | 9/1961 | Czuha | 204/195 W |
| 3,291,705 | 12/1966 | Hersch | 204/195 R |
| 3,432,403 | 3/1969 | Glass et al. | 204/1 T |

FOREIGN PATENT DOCUMENTS 1,174,312  12/1969  United Kingdom ........... 204/195 W

OTHER PUBLICATIONS

"XR Perfluorosulfonic Acid Membranes", New Product Information, Dupont de Nemours & Co., Oct., 1969, pp. 1-3.

Primary Examiner—T. Tung
Attorney, Agent, or Firm—Monte F. Mott; John R. Manning; Wilfred Grifka

[57] ABSTRACT

An improved flow-through electrolytic hygrometer is provided which utilizes a long lasting oxidation-resistant, hollow fiber formed of a persulfonic acid substituted polytetrafluoroethylene having closely spaced noble metal electrodes in contact with the inner and outer surfaces of the fiber. The fiber is disposed within a chamber such that the moisture-bearing gas passes in contact with at least one surface of the fiber. The electrodes are connected in series to a DC voltage supply and an ammeter. As the gas passes through the chamber, moisture absorbed into the wall of the fiber is electrolyzed to hydrogen and oxygen by the closely spaced electrodes. The amount of electricity required for electrolysis is proportional to the absorbed moisture and is observed on the ammeter.

13 Claims, 1 Drawing Figure

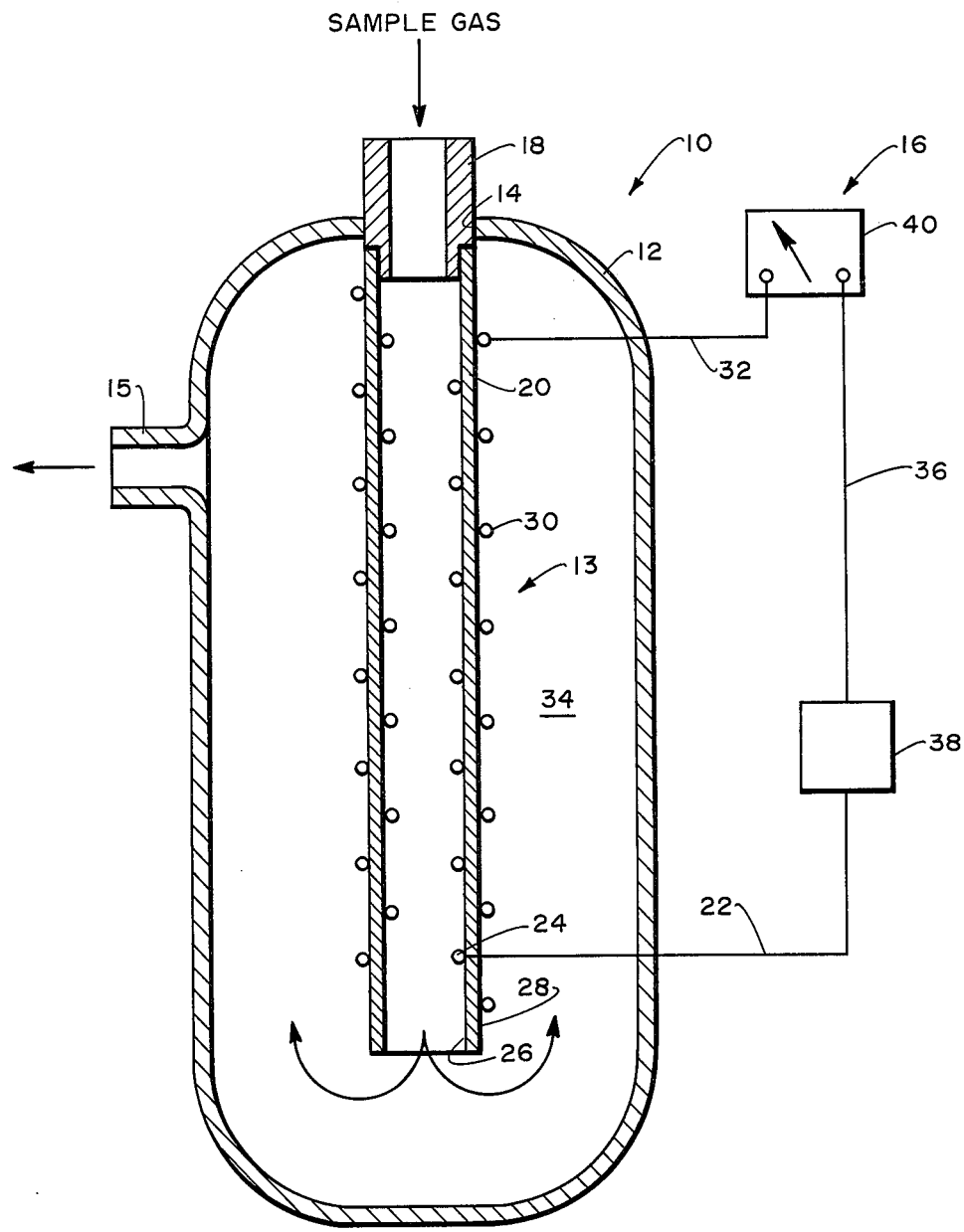

POLYMERIC ELECTROLYTIC HYGROMETER

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

BACKGROUND OF THE INVENTION

1. Field of the Invention

The present invention relates to measuring moisture content of non-condensible gases and vapors amperometrically, and, more particularly, to a solid polymeric eletrolytic hygrometer.

2. Description of the Prior Art

Hygrometers, which measure the humidity of a gas, may be characterized as being of two types: relative and absolute. The relative type, such as wet and dry bulb thermometers, require calibrations under various test conditions, are limited in dynamic range, especially in low moisture concentration environments. The absolute type, such as the electroyltic cell, have a great dynamic range in measurable moisture concentrations, as well as a great temperature and pressure range. The electrolytic cell gives an exact measure of the available water by elecrolyzing it to hyrogen and oxygen.

Current state-of-the-art hygrometers use the principles disclosed by F. A. Keidel in Anal. Chem. 31, No. 12, p. 2043, Dec. 1959. This hydrometer design consists of an electrolytic cell through which moist gases are drawn. The water vapor content of the gas is absorbed at the surface of a polyphosphoric acid film and electrolyzed to gaseous hydrogen and oxygen by means of closely-spaced noble metal electrodes.

The acid electrolyte in these hydrometers is a complex inorganic polymer of phosphorous pentoxide and meta-phosphoric acid that is a viscous liquid at ambient temperatures and has a vapor pressure estimated near 0.1 mm Hg. In accordance with Faraday's Law, the electrolysis of one gram equivalent weight of water (9.01g) theoretically requires 96,500 colombs of electricity. The voltage of the cell must be greater than 1.23V and in most cases is about 10 times this value. The current drawn by the electrolytic cell is a direct measure of the rate at which water is being electrolyzed, which in equilibrium conditions equals the rate at which water is being absorbed at the acid electrode interface. A knowledge of the gas flow rate and the current drawn by the cell gives an absolute and continuous measure of the humidity mixing ratio of the sampled gas.

A known problem area in the use of polyphosphoric acid as an electrolyte in a hygrometer sensor is that the material is a liquid that can move under high g loads, and would tend to evaporate, particularly under prolonged exposure to the hard vacuum of deep space. In addition, certain gases, such as ammonia, interfere with the absorption process and thus degrade the sensor operation.

Other hygrometers have been disclosed which utilize solids such as polystyrene to absorb water from an air sample. All disclosed solids can be oxidized, so that they decompose rather quickly and must be replaced frequently.

SUMMARY OF THE INVENTION

A long-lasting electrolytic hygrometer capable of use in substantially all gaseous environments has been developed in accordance with this invention. The hygrometer includes a solid, polymeric electrolyte, oxidatively resistant hygroscopic tube having a pair of closely spaced, high surface area electrodes in contact with the inner and outer wall surfaces of the tube. The tube is disposed in a flow-through container enclosure connected to an inlet thereof. As moisture containing gas flows into the inlet, the gas flows in contact with at least one surface, preferably both surfaces, of the tube and the moisture is absorbed therein. A series circuit connected to the electrodes contains a DC power supply and an ammeter. As the absorbed water is continuously electrolyzed to hydrogen and oxygen, the current is read and/or recorded by the meter.

The hygrometer of the invention is capable of a long service life and use in varied environments due to the use of a high molecular weight solid polymeric tubular film having ion exhange functionality which is resistant to oxidation and reduction environments and has the capability of absorbing moisture. High molecular weight polymeric materials have vapor pressures close to zero. Furthermore, since chemical stability is so good and stability to currents is so high, the hygrometer electrolyte element can be used for extended periods without deterioration. Furthermore, since the electrolyte is solid it is not effected by high g loads and the functionality being bound to the solid polymer structure is not effected by certain gases such as ammonia which have been found to interact with polyphosphate electrolytes in prior instruments. Moreover, the inert nature of the solid polymeric film allows it to be used with oxidative and reductive gases, which develop during the electrolysis reaction and the film must be able to withstand the effects of nacent oxygen developed during this reaction.

Preferred solid polymeric electrolytic tubular elements are formed of sulfonated aliphatic fluorocarbon polymers and especially Nafion which is a perfluorosulfonic acid substituted polytetrafluoroethylene in which each repeating unit has a molecular weight of about 1000 and has the following structure:

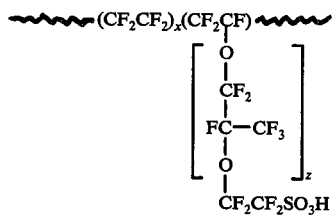

where $x$ and $z$ are integers such that the final polymer has a high molecular weight above 100,000 suitable 500,000 to 1,000,000 and $x$ and $z$ are integers such that the polymer contains a minimum sulfonic acid content of about 1.0 millequivalents/gram, suitably 1% to 1.5% millequivalents/gram.

Polymers having above structure are capable of withstanding the chemical environment of gases to be analyzed and the nacent oxygen developed during the electrolysis reaction. These polymers have superior mechanical strength, predictable dimensional changes, high electrical conductivity and are hydrogels having excellent water absorption characteristics. Films of this polymer have use as solid-polymer electrolytes in the electrolysis of salt to form chlorine gas and pure hydroxide. The polymers have demonstrated excellent chemical stability and can be used in electrolytic cells that pass currents as high as 10 amp/cm$^2$ at a temperature of 130° C for periods of up to five years. Wet Nafion polymers (20% water content) have an electrical resistance of about 1 ohm-cm. The vapor pressure is close to zero due to high molecular weight.

The tubular element may be disposed in the flow through container connected to the inlet and outlet of the container. However, for gas impermeable tubular elements such as Nafion, the tubular element is connected to only the inlet of the container such that the gas flows over both surfaces in order to assure adequate absorption and more optimum and accurate response of the system. The high surface area electrodes may be a spiral, braid or other configuration or may be in the form of an electrodeposited metal layer.

These and many other features and attendant advantages of the invention will become apparent as the invention becomes understood by reference to the following detailed description when considered in conjunction with the accompanying drawing.

BRIEF DESCRIPTION OF THE DRAWING

The FIGURE is a schematic view of an electrolytic hygrometer in accordance with the invention.

DESCRIPTION OF THE PREFERRED EMBODIMENT

Referring now to the FIGURE, the electrolytic hygrometer 10 generally includes a gas impervious flow-through vessel 12, an electrolytic hygrometer cell assembly 13 and a external power supply and measuring assembly 16. The vessel 12 has an inlet aperture 14 and an side outlet arm 15. An inlet fitting 18 is sealingly received in aperture 14 and the lower end of which is connected to the solid electrolyte hygrometer element 20. The lower end of the element 20 is held in place by means of conductor wire 22 which engages the internal spiral wound electrode 24 which is placed in firm engagement with the inner surface 26 of the element 20. The outer surface 28 of the element is engaged by spiral wound electrode element 30 which is connected to the external circuit 16 by means of conductor wire 32. Conductor wires 22, 32 sealingly penetrate the wall of the vessel 12 such that a gas-tight enclosure 34 is maintained. The external circuit 16 also includes a conductive member 36 joining power supply 38 in series circuit with the meter 40. The series circuit is completed by means of the electrodes 30, 24 when connected across the conductive path of the wall of tubular solid polymeric electrolyte element 20.

The electrolytic hygrometer of the invention is especially applicable to measurement of water content of gases at concentrations less than 1 ppm by volume up to about 1000 ppm. However higher concentrations can easily be measured. Many liquids can be analyzed after vaporization and other liquids and many solids can be analyzed by stripping with an inert gas. The outer vessel can be formed of any gas-impermeable material such as glass, or steel. The length and wall thickness of the tube is selected to provide an adequate diffusion path so that all moisture in the sample is absorbed during transit through the outer container. For example, approximately 2-3 inches of the Nafion tube having an inner diameter of 1.0 mm and an outer diameter of 3.0 mm is required at a usual flow rate of about 10 ml/min.

The cell must be operated at a minimum voltage of 2 volts, the decomposition voltage for water. At lower voltages no electrolysis of water takes place, regardless of its concentration in the wall of the fiber. The power source may be either a fixed voltage source such as an 11 volt battery or a line-operated direct current voltage supply can be utilized to provide the required voltage. An excess voltage can be applied to the cell to insure quantitative operation at low ranges. The flow circuit for the sample gas should include a conventional flow controller and a flow gauge such as a rotameter. In low pressure applications it is necessary to apply vacuum at the outlet in order to obtain sample flow.

Response time depends on thickness of the hollow fiber tube, applied cell voltage and electrode spacing. The shorter the electrode spacing, controlled by the wall thickness of the fiber, the faster the response time.

The electrolytic hygrometer of the invention can be used on a wide variety of gas samples such as nitrogen, hydrogen, air, carbon dioxide, helium, argon and many hydrocarbons. Gases such as chlorine, hydrogen chloride, sulfur dioxide and Phosgene can be utilized as long as the materials of construction are selected to be inert to these materials. Fluorinated hydrocarbons such as Freon refrigerants are easily analyzed after vaporization. The hygrometer of the invention is also applicable to basic material such as ammonia which are not analyzable with phosphoric acid electrolytic cells. Metal chips or other conducting particles should be avoided since they can anodically dissolve and cathodically redeposit as filaments which eventually short-circuit the electrodes. Such particles should be removed by use of a filter in the sampling circuit.

A prototype hygrometer was constructed from a glass enclosure in which was sealed a three inch length of Nafion hollow fiber having an inner diameter of 1.0 mm and an outer diameter of 1.3 mm. Noble metal platinum electrode coils were placed in contact with the inner and outer surfaces of the hollow fiber tube and the ends of the coils were connected in series to an 11 volt battery power supply and a microammeter. Air was flowed through the tube and into the outer glass enclosure at a rate of 10 ml/min. and the meter recording indicated the water concentration of the gas.

The electrolytic hygrometer of the invention can be applied to either batch-type of continuous measurements for a large variety of industrial and research analytical requirements. The instrument may be applied to analysis of inert blanketing gas for industrial processes, laboratory dry boxes, process gas streams and instrument air supplies. Volatile liquids can be analyzed after vaporization and the water content of higher boiling liquids can be analyzed after removing moisture by stripping with an inert gas.

It is to be realized that only preferred embodiments of the invention have been described and that numerous alterations substitutions and modifications are all permissable without departing from the spirit and scope of the invention as defined in the following claims.

What is claimed is:

1. An electrolytic hygrometer comprising in combination:

a closed sample container having an inlet and an outlet defining a sample gas flow path therebetween;

an oxidation-resistant, hygroscopic, gas-impermeable, solid persulfonic acid substituted polytetrafluoroethylene polymeric tube for absorbing moisture from the sample gas;

means mounting the tube within the container parallel to and within the flow path such that the sample gas flows in contact with the inner and outer surfaces of the tube;

a first electrode in contact with the inner surface of the tube;

a second counter-electrode in contact with the outer surface of the tube and opposed to the first electrode; and conductor means defining a series circuit with said electrodes including a DC power source capable of electrolyzing water absorbing by the tube and a meter for measuring the electrolyzing current.

2. A hygrometer according to claim 1 in which the polytetrafluoroethylene has a repeating unit of the formula:

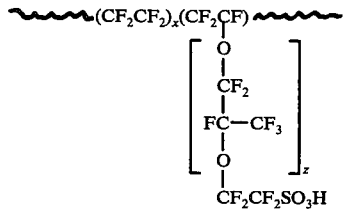

where x and z are integers such that the final polymer has a high molecular weight above 100,000 and x and z are integers such that the polymer contains a minimum sulfonic acid content of 1.0 millequivalents/gram.

3. A hygrometer according to claim 2 in which the tube has an outer diameter of no more than 3 mm.

4. A hygrometer according to claim 3 in which the tube has an inner diameter of no more than 1.0 mm.

5. A hydrometer according to claim 1 in which the tube has a first open end and a second open end, said first end being sealingly connected to said inlet.

6. A hygrometer according to claim 1 in which the electrodes are formed of nobel metal.

7. A hygrometer according to claim 6 in which the first electrode is a coiled wire in contact with the inner surface of the tube and the counterelectrode is a coiled wire in contact with the outer surface of the tube.

8. A method of amperometrically determining the water content of a gas comprising the steps of:

flowing a sample of the gas past the inner and outer surfaces of an oxidant-resistant, hygroscopic, solid persulfonic acid substituted polytetrafluoroethylene polymeric tube, having a first electrode in contact with the inner surface of the tube and a counter-electrode in contact with the outer surface of the tube;

absorbing water from the gas into the wall of the tube;

applying a DC potential to the electrodes to electrolytically decompose the absorbed water; and measuring the current required for the electrolytic decomposition.

9. A method according to claim 8 in which the polytetrafluoroethylene has a repeating unit of the formula:

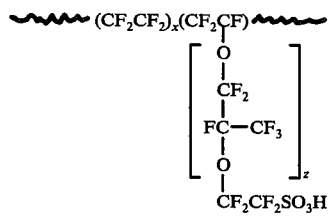

where x and z are integers such that the final polymer has a high molecular weight above 100,000 and x and z are integers such that the polymer contains a minimum sulforic acid content of 1.0 millequivalents/gram.

10. A method according to claim 8 in which the electrodes are formed of nobel metal.

11. A method according to claim 10 in which the first electrode is a coiled wire in contact with the inner surface of the tube and the counterelectrode is a coiled wire in contact with the outer surface of the tube.

12. A method according to claim 8 in which the tube has an outer diameter of no more than 3.0 mm.

13. A method according to claim 12 in which the tube has an inner diameter of no more than 1.0 mm.

* * * * *